United States Patent [19]

Heraly

[11] Patent Number: 4,605,007
[45] Date of Patent: Aug. 12, 1986

[54] TEMPORARY PACKAGE FOR AN ELECTRICAL COMPONENT
[75] Inventor: Neil H. Heraly, New Brighton, Minn.
[73] Assignee: Medtronic, Inc., Minneapolis, Minn.
[21] Appl. No.: 155,432
[22] Filed: Jun. 2, 1980
[51] Int. Cl.$^4$ ............................................. A61N 1/00
[52] U.S. Cl. ............................ 128/419 PT; 206/328; 206/333
[58] Field of Search ............... 206/328, 330, 331, 333; 324/158 P, 67; 128/419 P, 419 PT, 419 PG, 1 R

[56] References Cited

U.S. PATENT DOCUMENTS

| | | | |
|---|---|---|---|
| 2,856,449 | 10/1958 | Coler | 174/50.64 |
| 3,385,426 | 5/1968 | May et al. | 206/331 |
| 3,478,746 | 11/1969 | Greatbatch | 128/419 PG |
| 3,712,695 | 1/1973 | Kaye | 206/333 |
| 3,756,328 | 9/1973 | Cosier et al. | 206/328 |
| 4,238,030 | 12/1980 | Maylandt | 206/328 |

OTHER PUBLICATIONS

Medtronic Publication TC 68221R, Nov. 1968, 50 pp.
Cordis Publication 149-2340, Rev. 0, 1974, 15 pp.

Primary Examiner—William E. Kamm
Attorney, Agent, or Firm—Vidas & Arrett

[57] ABSTRACT

A temporary package for an electrical component including a container for housing the electrical component. The container is adapted to maintain a specialized internal environment until opened. Electrical communication may be established with the container housed electrical component without compromising the container internal environment. In a preferred embodiment, the electrical communication is established along an electrically conductive path extending between the container interior and exterior. The specialized environment may be a sterile internal condition with the container being formed of nested inner and outer trays each closed by a gas permeable closure through which sterilization is effected. The housed electrical component may be a signal generator, in which event its output signals are delivered to the container exterior without compromising the sterile condition within the container.

11 Claims, 5 Drawing Figures

TEMPORARY PACKAGE FOR AN ELECTRICAL COMPONENT

DESCRIPTION

1. Background of Prior Art

It is often necessary or desirable to maintain electrical components in a specialized environment following manufacture or at intermediate stages of manufacture. Such practices are common in the aerospace industry, the computer industry and the medical device industry, for example. One approach to environment maintenance has been to store such components within a temporary package which includes a container that maintains the specialized internal environment. This environment is often a sterile condition.

A specific example of an electrical component of the type described above is a body implantable signal generator, one type of which is a major component of the well-known cardiac pacemaker. Following manufacture, and prior to implantation, such generators are typically packaged in a container adapted to maintain a sterile internal condition during storage, shipment and intermediate handling. In the event that it is necessary or desirable to check the signal generator's output parameters, it has been necessary to open the temporary packaging thereby violating the internal sterile condition. In addition, recent signal generators have one or more programmable output parameters which can be externally reprogrammed after implantation. Such signal generators are inherently reprogrammable while in the temporary packaging. Heretofore, it has been necessary to remove the signal generator from the packaging, or at least open the packaging to expose the generator, to establish that a desired reprogramming has been effected or that extraneous signals have not resulted in an undesired reprogramming. To accomplish this without compromising the sterility of the signal generator is, at best, difficult. Most often signal generator sterility is intentionally compromised with the necessity of re-sterilizing the signal generator after repackaging.

2. Brief Summary of the Invention

The present invention provides a temporary package for an electrical component of the type in which a container houses the electrical component while maintaining a specialized internal environment until opened. Electrical communication may be established with the container housed electrical component without compromising the container internal environment. In a preferred embodiment, the package is adapted to contain a body implantable signal generator and to maintain a sterile internal condition, while closed, while delivering output signals from the housed signal generator to the container exterior without compromising the internal container sterility. The container may be formed as first and second nested trays with each tray being individually closed by a gas permeable closure member through which sterilization is effected. The output signals from the signal generator may be delivered over an electrically conductive path extending between the interior of the innermost nested tray to the exterior of the outermost tray. Contacts carried by the trays communicate with each other when the trays are in nested relation to complete the electrically conductive path. Terminals within the innermost tray are adapted to cooperate with the output connections of the signal generator and have a configuration dependent on whether that signal generator is unipolar or bipolar.

DETAILED DESCRIPTION OF THE INVENTION

Figure 1:
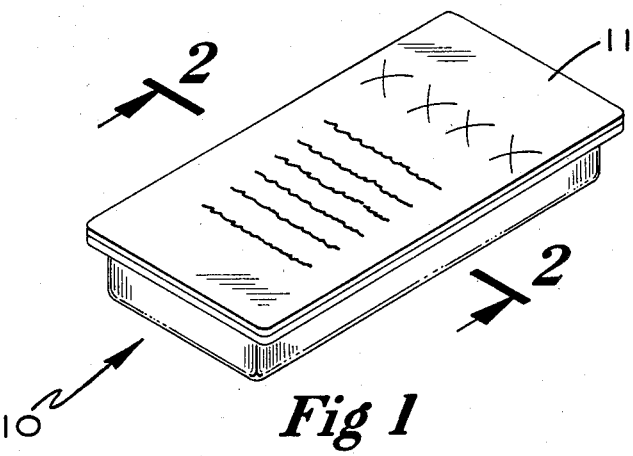
FIG. 1 is a perspective view of a temporary electrical component package by which the improvement of the present invention will be partially explained.

FIG. 1 is a perspective view of a temporary electrical component package to which the improvement of the present invention may be applied. The package of FIG. 1 may be adapted to house one or more electrical components and associated tools, leads, etc. Similarly, multiple components may be housed therein, dependent on the requirements at the ultimate location of component use. The package of FIG. 1 is of a type known to the prior art which will maintain a specialized internal environment. Within the context of a body implantable component, that environment will typically be a sterile condition. Specifically, when the component is a body implantable signal generator, the package of FIG. 1 may contain the signal generator and associated leads together with tools to facilitate the interconnection between the signal generator and signal conducting leads as well as tools to facilitate their implantation. In outward appearance, the package of FIG. 1 is formed of a container including a tray member generally designated at 10 and a gas permeable closure member 11. Closure member 11 allows sterilization of a housed electrical component, in known manner, while bearing indicia to identify the component, its manufacturer, its operating parameters, etc. Typically, sterilization of components housed within a package of the type illustrated in FIG. 1 is effected by placing the closed container within a pressurized atmosphere of ethylene oxide.

Figure 2:
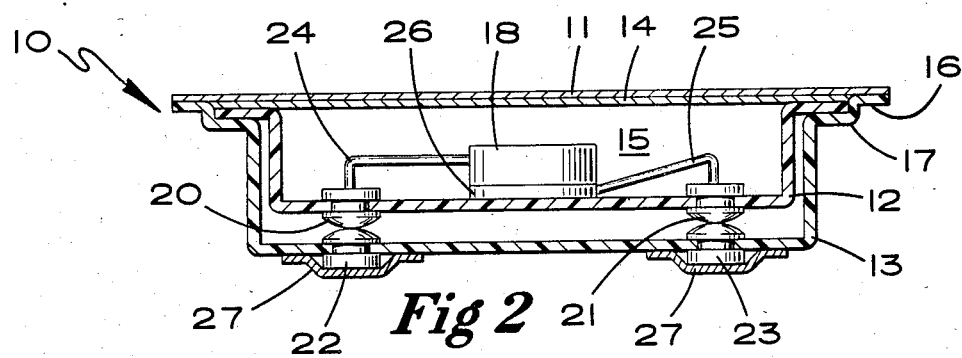
FIG. 2 is a cross-section taken along the line 2—2 in FIG. 1.

A preferred embodiment of the improvement of the present invention is illustrated in FIG. 2 which is a cross-section taken along the line 2—2 in FIG. 1. As shown in FIG. 2, the tray member 10 of the container is typically formed of inner and outer nesting trays 12 and 13, respectively. Innermost tray 12 is closed by a gas permeable closure member 14 while closure member 11 closes the entirety of the container, in known manner. Following sterilization, as described above, a sterile internal condition is maintained within the internal space 15 of tray 12. As illustrated in FIG. 2, a lip 16 around the upper part of the sidewall of tray 13 is adapted to cooperate with a lip 17 around the upper part of the sidewall of tray 12 to facilitate positioning of the tray 12 in nesting relation to the tray 13. The elements described to this point are known to the prior art and have been employed to contain an electrical component within the space 15 in a specialized atmosphere, a sterile condition, for example, during storage, shipping and intermediate handling. An electrical component 18 is illustrated within space 15 in FIG. 2.

Heretofore, electrical access to a component 18 within space 15 has required an opening of the closure members 11 and 14 thereby violating the specialized environment within space 15. Thus, after packaging, a rechecking of the parameters of a contained electrical component requires a repackaging of that component and re-establishment of the specialized environment—a potentially expensive operation. In addition, many electrical components for which it is necessary or desirable to maintain a specialized environment have externally programmable operating parameters. For example, it is desirable to maintain a body implantable signal generator in a sterilized condition until the generator is carried to the sterile field of the operating room for implantation. Recently, such generators are often externally programmable, particularly those that are intended for use for cardiac stimulation. Such generators may be reprogrammed within their packaging, prior to implant, with it being desirable to determine that the desired programming has been established without violation of the sterile condition in which they are housed. In addition, such signal generators may, under certain conditions, be susceptible to an extraneous reprogramming. It is desirable to have the facility to determine the programmed state of such signal generators, again without violating the sterile condition within which they are housed. The present invention provides this facility.

Still with reference to FIG. 2, the innermost nesting tray 12 is illustrated with contacts 20 and 21 extending from the space 15 to the exterior of the tray 12. Contacts 22 and 23 are carried by the tray 13 and positioned to establish an electrical communication with the contacts 20 and 21, respectively, when the tray 12 is in nesting relation to the tray 13. Contacts 20–23 may be formed of a conductive plastic or other conductive material molded or fitted through apertures within the trays 12 and 13 so as to provide contact surfaces on both the interior and exterior of the tray 12 and 13 while sealing the apertures through which they extend. An electrical conductor 24, which is in electrical communication with contact 20 extends from the contact 20 to an input-/output terminal of electrical component 18 in any desired manner. Similarly, an electrical conductor 25, which is in electrical communication with contact 21, extends from the contact 21 to an input/output connection of electrical component 18. In the event that electrical component 18 is of a type having an input/output connection at its outer surface, as is the case in a unipolar pulse generator for cardiac pacemaking, the conductor 25 may terminate in an electrically conductive pad 26 on which the electrical component 18 may rest with its externally carried electrical connection surface in contact with the pad 26 as illustrated in FIG. 2. The pad 26 may take the form of a molded plastic conductive material or any other suitable material.

As illustrated in FIG. 2, an electrical communication is established between the electrical component 18 within the interior space 15 of tray 12 to the contacts 22 and 23 at the outer surface of the tray 13. Test probes may be applied to the contacts 22 and 23 to determine the electrical parameters of the electrical component 18 within the space 15 without opening the package and thereby without violating the specialized atmosphere maintained within the space 15. Of course, as many conductive paths as are necessary to fully determine the parameters of a housed electrical component may be established. Also, when more than one electrical component is housed within the package, as many electrical paths as are necessary to fully determine the parameters of each may be established. Further, tray 12 may be configured so as to maintain each component 18 within a desired location within the space 15 of tray 12, in known manner. To eliminate the potential for shorting one conductive path to another, each of the contact surfaces on the outer surface of tray 13 may be provided with an insulating member 27 adhesively and removably secured to the exterior surface of the tray 13 to overlie the contacts.

Figure 3:
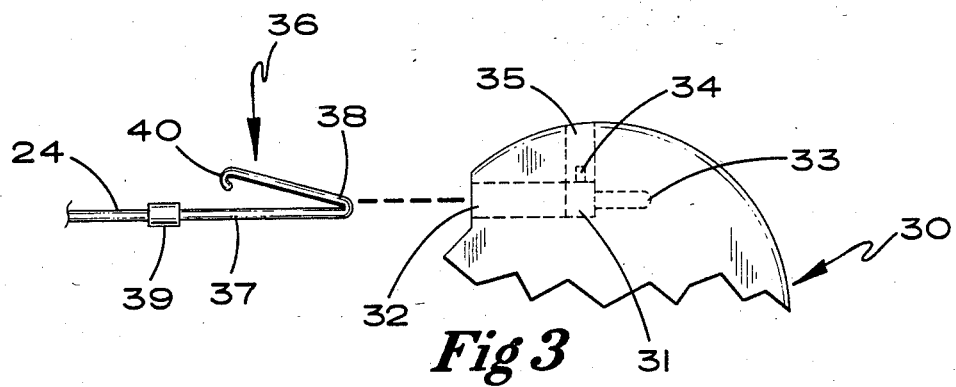
FIG. 3 is an exploded view that illustrates the interconnection between the improvement of the present invention and a particular electrical component to which the present invention has application.

Typically prior art signal generators, for example pulse generators intended for cardiac pacemaking, include a connector assembly for mechanically and electrically interconnecting the signal generator components to the output delivering lead. A typical connector assembly is illustrated in FIG. 3 and indicated generally at 30 and includes one or more terminal blocks 31 in electrical communication with the signal generating components and accessible via a receptable formed of a bore 32 and aperture 33, the bore 32 accepting a contact pin carried by the lead as well as a portion of the lead body with the pin extending through a bore in the terminal 31 into the aperture 33. A set screw 34, carried by the terminal 31, is accessible via a bore 35 to engage a pin within the bore in terminal 31 to mechanically engage the pin and assure a reliable electrical contact between that pin and the terminal 31.

The various bores, recesses, etc., of the connector assembly illustrated in FIG. 3 are often the most difficult to sterilize and are often the test sites for contamination testing. Accordingly, any electrical communication with the terminal 31 must be accomplished in a manner which does not unduly reduce the ability to sterilize the bore 32, the bore through the terminal 31 and the aperture 33. It is also desirable that the contact element establishing electrical contact with the terminal 31 be easily removable so as to not unnecessarily hamper removal of the unit from the inner area of 15 of tray 12 for use. Such a contact is illustrated at 36 in FIG. 3 carried at the end of and in electrical communication with the conductor 24 of FIG. 2. The contact 36 is formed of first and second legs 37 and 38 forming an acute angle which are insertable into the aperture 32 through the bore in the terminal 31 and into aperture 33 to establish an electrical contact with the terminal 31. In this position, an electrical communication is established between the terminal 31 and the contact 20 of tray 12 with which the conductor 24 cooperates. Further, this configuration does not fill the aperture 32, the bore in terminal 31 or the aperture 33 such that those areas may be sterilized by prior art methods, ethylene oxide, for example. Contact 36 may be formed of a wire crimped to the conducting portion of the conductor 24 as at 39 with the legs 37 and 38 being biased to maintain the position illustrated such that a mechanical force is exerted on the bore of terminal 31 when the clip 36 is inserted therein. The end of leg 38 may be folded back as illustrated at 40 to minimize the potential for the piercing of gloves or skin.

Figure 4:
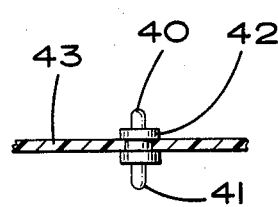
FIG. 4 illustrates an alternative to a portion of the embodiment illustrated in FIG. 2.
Figure 5:
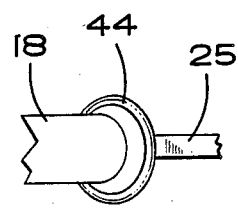
FIG. 5 illustrates an alternative to another portion of the embodiment illustrated in FIG. 2.

Obviously, many modifications and variations of the present invention are possible in light of the above teachings. For example, FIG. 4 illustrates an alternative to one or more of the contacts 20–23 of FIG. 2. FIG. 4 is an electrical feedthrough similar to that commonly employed in body implantable medical devices. It consists of pins 40 and 41 which are in electrical communication with each other and carried by an insulating housing 42. The housing 42 may cooperate with a wall 43 (which may correspond to a wall of either of trays 12 or 13) to seal that wall while electrically insulating that wall from the terminals 40 and 41. In some instances, the use of a feedthrough of the type illustrated in FIG. 4 may require the use of an electrical conductor with one or both of the pins 40 and 41. Further, FIG. 5 illustrates an alternative to the pad 26 illustrated in FIG. 2. Electrical component 18, having an electrical contact surface at its outer surface, may be electrically engaged via a clamp or clip 44 carried by a conductor 25. The clip 44 may take any convenient form capable of reliably but releasably engaging the exterior contact surface of the electrical component 18. Other configurations may be substituted for elements 26, 36 and 44, the particular configuration being a matter of choice, within the given constraints, as well as the requirements of the particular electrical components with which the elements are to cooperate. It is therefore to be understood that, within the scope of the appended claims, the invention may be practiced otherwise than as specifically described.

I claim:

1. In a temporary package for a body implantable signal generator of the type having a container housing a signal generator, the container including tray means and gas permeable closure means maintaining a sterile internal condition while closed, the improvement which comprises means for monitoring the operating parameters of said container housed signal generator at the tray means exterior without compromising internal container sterility including electrically conductive path means extending through said tray means to at least two electrical contact means at said tray means exterior and insulating means removably secured to said tray means exterior over said contact means.

2. The signal generator package of claim 1 wherein said tray means comprises a first tray nested within a second tray, each tray being closed by gas permeable closure means and said electrically conductive path means extending between the interior of said first tray to the exterior of said second tray.

3. The signal generator package of claim 2 wherein said electrically conductive path means comprises first electrical contact means carried at the exterior of said first tray and second electrical contact means carried at the interior of said second tray, said first and second electrical contact means establishing electrical communication therebetween when said first tray is nested within said second tray.

4. The signal generator package of claim 3 wherein said container housed signal generator is of the type having output contacts, said electrically conductive path means further comprising means extending from said first contact means contacts into the interior of said first tray and contacting said signal generator output contacts.

5. The signal generator package of claim 4 wherein at least one of said signal generator output contacts comprises receptacle means and terminal means within said receptacle means, said means extending from said first contact means contacts comprising means engageable with said terminal means through said receptacle means without filling said receptacle means.

6. The signal generator package of claim 5 wherein one of said signal generator output contacts comprises a contact surface generally at the surface of said signal generator, said means extending from said first contact means contacts comprising means electrically contacting said contact surface.

7. The signal generator package of claim 6 wherein said means adapted to contact said contact surface comprises conductive clip means.

8. The signal generator package of claim 6 wherein said means contacting said contact surface comprises conductive pad means.

9. The signal generator package of claim 4 wherein one of said signal generator output contacts comprises a contact surface generally at the surface of said signal generator, said means extending from said first contact means contacts comprising means electrically contacting said contact surface.

10. The signal generator package of claim 9 wherein said means contacting said contact surface comprises conductive clip means.

11. The signal generator package of claim 9 wherein said means contacting said contact surface comprises conductive pad means.

* * * * *